(12) United States Patent
Arnold et al.

(10) Patent No.: US 6,500,821 B1
(45) Date of Patent: Dec. 31, 2002

(54) 4-AMINO-1-ARYL-1,5-DIHYDROPYRROL-2-ONES AND PROCESS FOR MAKING

(75) Inventors: Thomas Arnold, Radebeul; Klaus Unverferth, Dresden; Hans-Joachim Lankau, Einböhla; Angelika Rostock, Radebeul; Christine Tober, Weinböhla; Chris Rundfeldt, Coswig; Reni Bartsch, Ottendorf-Okrilla, all of (DE)

(73) Assignee: Arzneimittelwerk Dresden GmbH, Radebeul (DE)

( * ) Notice: Subject to any disclaimer, the term of this patent is extended or adjusted under 35 U.S.C. 154(b) by 59 days.

(21) Appl. No.: 09/652,488

(22) Filed: Aug. 31, 2000

(30) Foreign Application Priority Data

Sep. 16, 1999 (DE) .......................................... 199 44 332

(51) Int. Cl.⁷ .................... C07D 207/36; C07D 413/04; A61K 31/402; A61P 25/08; A61P 28/22
(52) U.S. Cl. .............................. 514/217.08; 514/231.5; 514/252.13; 514/317; 514/422; 540/602; 544/141; 544/372; 546/208; 548/550
(58) Field of Search .......................... 548/550; 544/141, 544/372; 546/208; 540/602; 514/217.08, 231.5, 252.13, 317, 422

(56) References Cited

U.S. PATENT DOCUMENTS 4,511,568 A    4/1985    Bare et al. .................. 514/293

FOREIGN PATENT DOCUMENTS

GB    1323 020    *    7/1973

* cited by examiner

*Primary Examiner*—Richard L. Raymond
*Assistant Examiner*—Venkataraman Balasubramanian
(74) *Attorney, Agent, or Firm*—Fulbright & Jaworski L.L.P.

(57) ABSTRACT

The invention relates to 1,5-dihydropyrrol-2-ones of Formula 1 which contain an aryl radical in the 1-position and a secondary amine radical in the 4-position, to a process for making and for a process to treat various forms of epilepsies and of states of anxiety and tension.

11 Claims, No Drawings

4-AMINO-1-ARYL-1,5-DIHYDROPYRROL-2-ONES AND PROCESS FOR MAKING

FIELD OF THE INVENTION

The invention relates to 1,5-dihydropyrrol-2-ones which contain a secondary amine radical in the 4-position and an aryl radical in the 1-position, to a process for their preparation, and to a process for their use as medicaments, specifically for the treatment of epilepsies of various forms and for the treatment of states of anxiety and tension.

BACKGROUND

Unsubstituted 1-phenyl-1,5-dihydropyrrol-2-one was described in 1981 by a Japanese group [K. Tabei et al., Heterocycles 1981, 16, 795]. 1,5-dihydropyrrol-2-ones having aryl substituents in the 1-position and primary amines as substituents in the 4-position have been described by Lonza AG in German patent No. 2,214,488. No biological activity of the compounds described therein was mentioned or suggested.

Compounds which are alkoxy-substituted in the 4-position, such as, for example, 4-ethoxy-1-phenyl-1,5-dihydropyrrol-2-one, are known [T. Nishio et al., J. Chem. Soc. Perkin Trans. 1, 1992, 899]. Also for these compounds, no biological activity has been disclosed.

1,5-dihydropyrrol-2-ones having a secondary amine radical in the 4-position and an aryl radical in the 1-position have so far not been described.

Epilepsy is a behavioral change in the form of convulsions. The cause is short-term, extremely strong neuronal discharges of the brain. Altogether, about 5% of all people suffer an epileptic attack in their life; 1% suffer from epilepsy.

Fundamentally, two factors are to be considered for the genesis of convulsions, pathological discharges in groups of nerve cells and/or absent stimulus limitation which makes possible a spread of the pathological stimulation, i.e. there is an increased instability of the cell membrane potential with a tendency for spontaneous electrical discharges.

Only about 60–80% of patients currently become attack-free under medicinal treatment. Certain forms of epilepsy, however, can still not be treated adequately. In addition, undesired side effects, such as neurotoxicity and idiosyncrasy, can occur through the administration of anticonvulsants that are on the market.

Anxiety states and tension of differing etiology and intensity cannot be currently satisfactorily treated in all cases. Since approximately 1960, benzodiazepine derivatives have been employed as a matter of priority for the treatment of anxiety states and tension. Substances generally having such a profile have a calming and emotion-dampening action. In the short term, these medicaments can be of great help, but even in therapeutic doses side effects such as sedation, drowsiness and decreases responsiveness will occur.

There can be an adverse effect on mental processes due to sedation. In some cases, ataxia and coordination disorders can be observed, which affect performance.

On continuous use, these benzodiazepine compounds lead to habituation effects, i.e. the so-called tolerance. The efficacy of the preparation decreases and the dose has to be increased. A psychological dependence, and even a physiological dependence, can develop. Hence, complicated withdrawal phenomena will occur when withdrawal is attempted.

The most important representatives of the anxiolytics introduced onto the market are the active compounds diazepam, clonazepam and medazepam.

To achieve an anxiolytic action of diazepam, plasma concentrations of 300 to 400 ng/ml are necessary. The side effects mentioned, such as sedation and psychomotor disorders, which are manifested in daytime sedation, drowsiness and restricted attentiveness and responsiveness, also occur, however, at the same concentrations. On account of the long half-life of diazepam and clonazepam, severe "hang-over" effects occur, which are likewise associated with drowsiness, impairment of intellectual and motor capacities, and prolonged reaction time. The anxiolytic action of clonazepam is masked by the sedating or hypnotic action. High doses of medazepam are also associated with hypnotic, muscle-relaxing phenomena. All three medicaments potentiate the action of numerous centrally acting pharmaceuticals and of alcohol. In these cases, effects can occur which are barely noticeable after administration of the individual substances.

Until now, attempts to achieve a satisfactory therapeutic standard in the case of relatively long-lasting states of anxiety have been unsuccessful. A therapy-outlasting action of anxiolytic medicaments is presently also not adequately ensured.

DESCRIPTION OF THE INVENTION

It is an object of the present invention to provide compounds having favorable pharmacological properties, which can be employed as medicaments, in particular for the treatment of epilepsy.

It is a further object of the present invention to provide medicaments for the treatment of different states of anxiety and tension and which have a great therapeutic spectrum.

According to the present invention, these novel medicaments are 4-amino-1-aryl-1,5-dihydropyrrol-2-ones of Formula 1

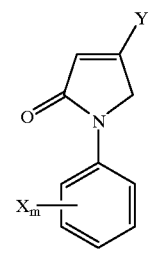

(1)

where

X is hydrogen, halogen, a $C_{1-4}$-alkyl, $C_{1-4}$-alkoxy, trifluoromethyl or trifluoromethoxy, nitro, or amine residue;

Y is a secondary amine residue, such as, for example, a morpholine, piperidine, 2-methylpiperidine, 3-methylpiperidine, 4-methylpiperidine, pyrrolidine, 4-methylpiperazine, azepam, diethylamino, bis(methoxyethyl)amine residue; and m is a cardinal number between 1 and 3.

Examples of compounds of Formula 1 include:

1-(2-chlorophenyl)-4-morpholin-4-yl-1,5-dihydropyrrol-2-one;

1-(3-methylphenyl)-4-morpholin-4-yl-1,5-dihydropyrrol-2-one;

1-(4-fluorophenyl)-4-morpholin-4-yl-1,5-dihydropyrrol-2-one;

1-(4-chlorophenyl)-4-morpholin-4-yl-1,5-dihydropyrrol-2-one;

1-(4-bromophenyl)-4-morpholin-4-yl-1,5-dihydropyrrol-2-one;
1-(4-methylphenyl)-4-morpholin-4-yl-1,5-dihydropyrrol-2-one;
1-(4-methoxyphenyl)-4-morpholin-4-yl-1,5-dihydropyrrol-2-one;
4-morpholin-4-yl-1-(4-trifluoromethylphenyl)-1,5-dihydropyrrol-2-one;
4-morpholin-4-yl-1-(4-trifluoromethoxyphenyl)-1,5-dihydropyrrol-2-one;
1-(3-chloro-4-fluorophenyl)-4-morpholin-4-yl-1,5-dihydropyrrol-2-one;
4-morpholin-4-yl-1-(3,4, 5-trimethoxyphenyl)-1,5-dihydropyrrol-2-one;
1-(3-methylphenyl)-4-piperidin-1-yl-1,5-dihydropyrrol-2-one;
1-(4-fluorophenyl)-4-piperidin-1-yl-1,5-dihydropyrrol-2-one;
1-(4-chlorophenyl)-4-piperidin-1-yl-1,5-dihydropyrrol-2-one;
1-(4-methylphenyl)-4-piperidin-1-yl-1,5-dihydropyrrol-2-one;
1-(3-chloro-4-fluorophenyl)-4-piperidin-1-yl-1,5-dihydropyrrol-2-one;
1-(4-chlorophenyl)-4-pyrrolidin-1-yl-1,5-dihydropyrrol-2-one;
1-(4-chlorophenyl)-4-(4-methylpiperidin-1-yl)-1,5-dihydropyrrol-2-one;
1-(4-chlorophenyl)-4-(3-methylpiperidin-1-yl)-1,5-dihydropyrrol-2-one;
1-(4-chlorophenyl)-4-(2-methylpiperidin-1-yl)-1,5-dihydropyrrol-2-one,
1-(4-chlorophenyl)-4-(4-methylpiperazin-1-yl)-1,5-dihydropyrrol-2-one;
1-(4-chlorophenyl)-4-azepam-1-yl-1,5-dihydropyrrol-2-one;
1-(4-chlorophenyl)-4-(diethylamino)-1,5-dihydropyrrol-2-one;
1-(4-chlorophenyl)-4-(bis(methoxyethyl)amino)-1,5-dihydropyrrol-2-one; and
4-morpholin-4-yl-1-phenyl-1,5-dihydropyrrol-2-one.

Compounds of Formula 1 are prepared by the substitution of compounds of Formula 2 by the corresponding amines.

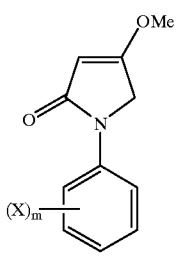

(2)

where

X is hydrogen, halogen, a $C_{1-4}$-alkyl, $C_{1-4}$-alkoxy, trifluoromethyl or trifluoromethoxy, nitro, or amine residue; and m is a cardinal number between 1 and 3.

Compounds of Formula 2 are obtained by heating 4-(arylamino)-3-methoxybut-2-enoic esters in an organic solvent, preferably acetic acid, at boil for 1–6 hours.

4-(arylamino)-3-methoxybut-2-enoic esters can be obtained from 4-haloacetoacetic esters by known methods.

Alternatively, compounds of Formula 3 can be condensed with the corresponding amines.

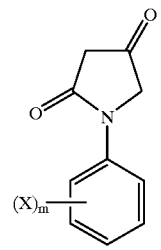

(3)

where

X is hydrogen, halogen, a $C_{1-4}$-alkyl, $C_{1-4}$-alkoxy, trifluoromethyl or trifluoromethoxy, nitro, or amine residue; and m is a cardinal number from 1 to 3.

Compounds of Formula 3 are synthesized by starting from known N-aryl-substituted glycine esters, analogously to the description by Mulholland, T. P. C.; Foster, R., Haydock, D. B.; J. Chem. Soc., Perkin Trans. 1 1972, 17, 2121–8.

The active compounds according to the present invention are suitable for preparing pharmaceutical compositions that comprise at least one of the compounds of Formula 1.

The compositions can be administered, for example, parenterally (such as intravenously, intramuscularly or subcutaneously) or orally.

The forms of administration can be prepared by processes which are customary and generally known in the pharmaceutical practice, using customary pharmaceutical vehicles and excipients.

The compounds according to the present invention have strong pharmacological activity.

Anticonvulsive Activity

Compounds according to the present invention were tested in vivo for their anticonvulsive action as shown in Table 1 in mice by i.p. administration, or in rats administered orally according to the internationally customary standard (Pharmac. Weekblad, Sc.Ed. 14 132 (1992) and Antiepileptic Drugs, Third Ed., Raven Press, New York 1989).

Analogous results were obtained for oral action. For example, for the compound 1-(4-chlorophenyl)-4-morpholin-4-yl-1,5-dihydropyrrol-2-one, in the rat in maximal electroshock the $ED_{50}$ (p.o.) was determined to be 19 mg/kg, in the pentetrazol convulsion model, the $ED_{50}$ (p.o.) was determined to be 11 mg/kg and for the neurotoxicity, the $NT_{50}$ was determined to be >500 mg/kg.

TABLE 1

Anticonvulsive action of selected 1,5-dihydropyrrol-2-ones of Formula 1

| Compound[1] | log P[2] | Test[3] | Dose[4] | Action[5] |
|---|---|---|---|---|
| 1 | n | MES | 100 | 0 |
|  |  | PTZ | 100 | 0 |
| 2 | 1.46 | MES | 100 | 33 |
|  |  | PTZ | 300 | 100 |
| 3 | n | MES | 100 | 50 |
|  |  | PTZ | 100 | 33 |
| 4 | 1.91 | MES | 300 | 0 |
|  |  | PTZ | 30 | 100 |
|  | 2.16 | MES | 100 | 33 |

TABLE 1-continued

Anticonvulsive action of selected 1,5-dihydropyrrol-2-ones of Formula 1

| Compound[1] | log P[2] | Test[3] | Dose[4] | Action[5] |
|---|---|---|---|---|
| 5 | | PTZ | 100 | 100 |
| | 1.42 | MES | 300 | 100 |
| 6 | | PTZ | 100 | 100 |
| | 0.74 | MES | 300 | 0 |
| 7 | | PTZ | 300 | 80 |
| | n | MES | 100 | 66 |
| 8 | | PTZ | 100 | 100 |
| | 2.45 | MES | 100 | 100 |
| 9 | | PTZ | 10 | 50 |
| | 2.19 | MES | 100 | 100 |
| 10 | | PTZ | 100 | 100 |
| | n | MES | 300 | 0 |
| 11 | | PTZ | 300 | 66 |
| | 2.66 | MES | 300 | 0 |
| 12 | | PTZ | 300 | 0 |
| | 2.35 | MES | 300 | 0 |
| 13 | | PTZ | 300 | 0 |
| | 3.06 | MES | 100 | 100 |
| 14 | | PTZ | 100 | 100 |
| | 2.62 | MES | 100 | 100 |
| 15 | | PTZ | 100 | 100 |
| | n | MES | 300 | 100 |
| 16 | | PTZ | 300 | 0 |
| | 2.60 | MES | 300 | 66 |
| 17 | | PTZ | 300 | 0 |
| | n | MES | 100 | 66 |
| 18 | | PTZ | 100 | 66 |
| | 3.58 | MES | 300 | 0 |
| 19 | | PTZ | 100 | 40 |
| | n | MES | 300 | 66 |
| 20 | | PTZ | 100 | 40 |
| | n | MES | 100 | 66 |
| 21 | | PTZ | 100 | 100 |
| | 3.40 | MES | 300 | 100 |
| 22 | | PTZ | 300 | 100 |
| | n | MES | 300 | 50 |
| 23 | | PTZ | 300 | 66 |
| | n | MES | 300 | 33 |
| 24 | | PTZ | 300 | 66 |
| | n | MES | 100 | 40 |
| 25 | | PTZ | 100 | 66 |
| Comparison substances | | MES | 100 | 100 |
| Carbamazepin | | PTZ | 100 | 0 |
| Valproate | | MES | 100 | 0 |
| | | PTZ | 100 | 30 |

Footnotes
[1] Numbering of the compounds corresponding to the examples in Table 4
[2] Octanol/water partition coefficient, n = not measured
[3] Mouse i.p.: MES = maximal electroshock, PTZ = s.c. pentetrazole
[4] in mg/kg
[5] in % of the protected animals It can be seen from Table 1 that the compounds of the invention have anticonvulsive action and exhibit little if any neurotoxicity. It has also been surprisingly found that the compounds of Formula 1 have considerable anxiolytic action in the animal experiment, without any sedating effects.

Anxiolytic Activity

Compounds of Formula 1 have also been investigated to determine their effects in models for the investigation of the action against states of anxiety. The animals were exposed to different conflict situations and the effect, for example of the compound 1-(4-chlorophenyl)-4-morpholine-4-yl-1,5-dihydropyrrol-2-one (Example 4), was measured.

Investigation of the Inhibition of Anxiety by the Vogel Conflict Test

In this model, continuous access to drinking water is withheld from rats for a certain time. After this period, free access is given to drinking water, but is coupled with a mild electrical stimulation. The conflict for the animals is between accepting the electrical stimulation or going without a drink.

The reactions to a conflict situation of this type are similar to the secondary phenomena of anxiety in man. The resulting avoidance reactions can be suppressed by anxiolytic substances. As a measure of the anxiolytic action, the number of tolerated current pulses of the animals treated with the test substance is assessed in comparison to the vehicle-treated control group. The experimental results obtained are shown in Table 2.

TABLE 2

Anxiolytic action of substances in the Vogel Conflict Test/rat
x ± SEM; *p < 0.05, ** p < 0.01

| Substance | mg/kg p.o. | Changed number of impulses to the control in % |
|---|---|---|
| Control | — | 100 |
| Compound 4 | 3 | 102 |
| | 10 | 174 |
| Control | — | 100 |
| Diazepam | −0.1 | 94 |
| | 0.3 | 114 |
| | 1.0 | 148 |
| | 3.0 | 167 |
| Control | — | 100 |
| Clonazepam | 0.1 | 122 |
| | 0.3 | 128 |
| | 1.0 | 173 |
| Control | — | 100 |
| Medazepam | 0.3 | 100 |
| | 1.0 | 131 |
| | 3.0 | 78 |

For the compound of Example 4, even from 10 mg/kg p.o. an anxiolytic action was detected.

Equally effective doses of diazepam and clonazepam are 1 to 3 mg/kg p.o. and 1 mg/kg p.o., respectively. It was not possible to detect for medazepam an action in the dose range from 0.3 to 3 mg/kg p.o.

Untreated animals drink significantly less, which means that they are more anxious than animals which are treated with anxiety-inhibiting substances. The compound of Example 1 increases the number of electrical stimulations significantly tolerated from a dose of 3 mg/kg orally. This effect confirms the good anxiolytic action of the compounds of Formula 1. Thus the compounds of Formula 1 are shown to have an anxiety inhibiting effect, particularly in conflict situations.

Investigation of the Inhibition of Anxiety in the Elevated Maze

In this model, mice are placed in an elevated passage system with open and closed arms as described by Pellow, S., Chopin, P., File S. E., Briley, M.: Validation of open: closed arm entries in an elevated plus-maze as a measure of anxiety in rats. J. of Neuroscience Methods 14: 149–167, 1985; Hogg, S.: A review of the validity and variability of the elevated plus-maze as an animal model of anxiety. Pharmacology Biochemistry and Behavior: 21–30, 1996. Untreated animals repeatedly try the closed passages. The inhibition of anxiety is measured by the length of stay in the open arms as a percentage of the total length of stay. Treatments with the compounds of Formula 1 increase the length of stay in the open arms as a percentage, as can be seen from Table 3.

TABLE 3

Anxiolytic action of substances in the elevated maze test/mouse

| Treatment | | Activity in % |
|---|---|---|
| Control: | | 100 |
| Compound 4: | 1 mg/kg | 128 ($p < 0.05$) |
| | 3 mg/kg | 110 |
| Control: | | 100 |
| Compound 4: | 10 mg/kg | 158 ($p < 0.05$) |
| | 30 mg/kg | 129 |

Following intraperitoneal administration of the compound of Example 4, the proportionate length of stay in the open arms is significantly increased. Compared to customary anxiolytics, compounds of Formula 1 have a considerably wider therapeutic spectrum. In the Vogel Conflict Test and in the elevated maze test, for example, the therapeutic index for compound 4 is >50. In contrast, the therapeutic index of diazepam in the Vogel Conflict Test is 13.

The following examples illustrate the invention in more detail.

General Procedure for Preparing the Compounds of Formula 1 and Their Tautomers According to Table 4

EXAMPLES 1–25

30.0 mmol of the compound of Formula (2) (Process A) or the compound of Formula (3) (Process B) are dissolved in the appropriate amine, preferably in 5–10 ml per g of the compound of Formula (2), and admixed with the appropriate amine hydrochloride, preferably 1–3 g, and the mixture is heated. After 4–12 hours at 100–150° C., the reaction solution is cooled and the crystalline product is filtered off. Amine-hydrochloride can be removed by washing with water, and the resulting crude product is recrystallized from a suitable organic solvent, preferably acetic acid and isopropanol.

Alternatively, the crude product can also be purified by chromatography.

TABLE 4

4-amino-1-aryl-1,5-dihydropyrrol-2-ones, Examples 1–25

| Compound | X | Y | Process/Yield in (%) | m.p. (° C.) | Recrystallization from: |
|---|---|---|---|---|---|
| 1 | 2-Cl | morpholine | B 22 | 154–156 | Isopropanol |
| 2 | 3-Me | morpholine | A 18 | 121–123 | Chromatography |
| 3 | 4-F | morpholine | B 37 | 226–229 | Isopropanol |
| 4 | 4-Cl | morpholine | A 84 | 238–241 | Acetic acid |
| 5 | 4-Br | morpholine | A 36 | 230–233 | Toluene |
| 6 | 4-Me | morpholine | A 50 | 214–217 | Without recrystallization |
| 7 | 4-OMe | morpholine | A 37 | 198–202 | Isopropanol |
| 8 | 4-CF$_3$ | morpholine | A 54 | 205–207 | Acetic acid |
| 9 | 4-OCF$_3$ | morpholine | A 49 | 148–153 | Without recrystallization |
| 10 | 3-Cl-4-F | morpholine | A 51 | 162–166 | Without recrystallization |
| 11 | 3,4,5-(OMe)$_3$ | morpholine | A 54 | 179–182 | Isopropanol |
| 12 | 3-Me | piperidine | B 15 | 117–123 | Without recrystallization |
| 13 | 4-F | piperidine | B 14 | 214–216 | Chromatography |
| 14 | 4-Cl | piperidine | A 60 | 20–212 | Without recrystallization |
| 15 | 4-Me | piperidine | A 68 | 174–177 | Without recrystallization |
| 16 | 3-Cl-4-F | piperidine | A 63 | 195–196 | Chromatography |
| 17 | 4-Cl | pyrrolidine | A 51 | 223–227 | Without recrystallization |
| 18 | 4-Cl | 4-Me-piperidine | A 57 | 194–196 | Acetic acid |
| 19 | 4-Cl | 3-Me-piperidine | B 19 | 188–189 | Isopropanol |
| 20 | 4-Cl | 2-Me-piperidine | B 5 | 181–185 | Chromatography |
| 21 | 4-Cl | 4-methyl-piperazine | A 42 | 194–197 | Chromatography |
| 22 | 4-Cl | Azepam | B 30 | 182–185 | Isopropanol |
| 23 | 4-Cl | Diethylamine | A 55 | 165–168 | Acetic acid |
| 24 | 4-Cl | Bis(methoxyethyl)amine | B 6 | 189–195 | Chromatography |
| 25 | H | morpholine | B 25 | 161–164 | Chromatography |

What is claimed is:

1. A compound of Formula 1

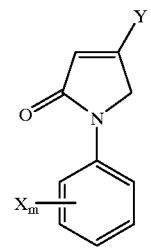

(1)

where
x is hydrogen, a halogen, C$_{1-4}$-alkyl, C$_{1-4}$-alkoxy, trifluoromethyl or trifluoromethoxy, nitro, or amino group;
Y is a secondary amino group, selected from the group consisting of, a morpholine, piperidine, 2-methylpiperidine, 3-methylpiperidine, 4-methylpiperidine, pyrrolidine, 4-methylpiperazine, azepam, diethylamine, bis(methoxyethyl)amine; and
m is a cardinal number between 1 and 3.

2. The following specific compounds of claim 1:

1-(2-chlorophenyl)-4-morpholin-4-yl-1,5-dihydropyrrol-2-one;
1-(3-methylphenyl)-4-morpholin-4-yl-1,5-dihydropyrrol-2-one;

1-(4-fluorophenyl)-4-morpholin-4-yl-1,5-dihydropyrrol-2-one;
1-(4-chlorophenyl)-4-morpholin-4-yl-1,5-dihydropyrrol-2-one;
1-(4-bromophenyl)-4-morpholin-4-yl-1,5-dihydropyrrol-2-one;
1-(4-methylphenyl)-4-morpholin-4-yl-1,5-dihydropyrrol-2-one;
1-(4-methoxyphenyl)-4-morpholin-4-yl-1,5-dihydropyrrol-2-one;
4-morpholin-4-yl-1-(4-trifluoromethylphenyl )-1,5-dihydropyrrol -2-one;
4-morpholin-4-yl-1-(4-trifluoromethoxyphenyl)-1,5-dihydropyrrol-2-one;
1-(3-chloro-4-fluorophenyl)-4-morpholin-4-yl-1,5-dihydropyrrol-2-one;
4-morpholin-4-yl-1-(3,4,5-trimethoxyphenyl)-1,5-dihydropyrrol-2-one;
1-(3-methylphenyl)-4-piperidin-1-yl-1,5-dihydropyrrol-2-one;
1-(4-fluorophenyl)-4-piperidin-1-yl-1,5-dihydropyrrol-2-one;
1-(4-chlorophenyl)-4-piperidin-1-yl-1,5-dihydropyrrol-2-one;
1-(4-methylphenyl)-4-piperidin-1-yl-1,5-dihydropyrrol-2-one;
1-(3-chloro-4-fluorophenyl)-4-piperidin-1-yl-1,5-dihydropyrrol-2-one;
1-(4-chlorophenyl)-4-pyrrolidin-1-yl-1,5-dihydropyrrol-2-one;
1-(4-chlorophenyl)-4-(4-methylpiperidin-1-yl)-1,5-dihydropyrrol-2-one;
1-(4-chlorophenyl)-4-(3-methylpiperidin-1-yl)-1,5-dihydropyrrol-2-one;
1-(4-chlorophenyl)-4-(2-methylpiperidin-1-yl)-1,5-dihydropyrrol-2-one;
1-(4-chlorophenyl)-4-(4-methylpiperazin-1-yl)-1,5-dihydropyrrol-2-one;
1-(4-chlorophenyl)-4-azepam-1-yl-1,5-dihydropyrrol-2-one;
1-(4-chlorophenyl)-4-(diethylamino)-1,5-dihydropyrrol-2-one;
1-(4-chlorophenyl)-4-(bis(methoxyethyl)amino)-1,5-dihydropyrrol-2-one; and
4-morpholin-4-yl-1-phenyl-1,5-dihydropyrrol-2-one.

3. A process for preparing a compound of claim 1, which comprises reacting a compound of Formula 2

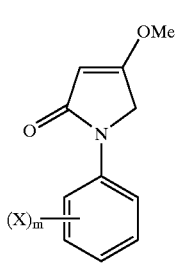

(2)

where
X is hydrogen, a halogen, $C_{1-4}$-alkyl, $C_{1-4}$-alkoxy, trifluoromethyl or trifluoromethoxy, nitro, or amino group; and
m is a cardinal number between 1 and 3,
with a secondary amino groups, selected from the group consisting of, morpholine, piperidine, 2-methylpiperidine, 3-methylpiperidine, 4-methylpiperidine, pyrrolidine, 4methylpiperazine, azepam, diethylamine, and bis (methoxyethyl)amine or said secondary amine hydrochloride.

4. The process of claim 3, wherein said secondary amino group is selected from the group consisting of morpholine, piperidine, 2-methylpiperidine, 3-methylpiperidine, 4methylpiperidine, pyrrolidine, 4-methylpiperazine, azepam, diethylamine, and bis(methoxy-ethyl)amine or said secondary amine hydrochloride.

5. Process for preparing a compound of claim 1, which comprises reacting a compound of Formula 3

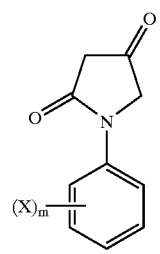

(3)

where
X is hydrogen, halogen, a $C_{1-4}$-alkyl, $C_{1-4}$-alkoxy, trifluoromethyl or trifluoromethoxy, nitro, or amino group, and
m is a cardinal number from 1 to 3,
with a secondary amino group selected from the group consisting of, morpholine. piperidine, 2-methylpiperidine, 3-methylpiperidine, 4methylpiperidine, pyrrolidine, 4-methylpiperazine, azepam, and diethylamine, bis (methoxyethyl)amine or said secondary amine hydrochloride.

6. The process of claim 5, wherein said secondary amino group is selected from the group consisting of morpholine, piperidine, 2-methylpiperidine, 3-methylpiperidine, 4-methylpiperidine, pyrrolidine, 4-methylpiperazine, azepam. and diethylamine, bis(methoxy-ethyl)amine or said secondary amine hydrochloride.

7. A pharmaceutical composition, which comprises at least one compound of Formula 1 as an active ingredient and a physiologically acceptable excipient and/or vehicle.

8. A pharmaceutical composition, which comprises as active ingredient, at least one compound of claim 2, and a physiologically acceptable excipient and/or vehicle.

9. A process for preparing a pharmaceutical composition compound of claim 1 which comprises admixing at least one compound of claim 1 with a pharmaceutically acceptable excipient and/or vehicle.

10. A process for the treatment of epilepsy and anxiety states, which comprises administering to a patient in need therefor an effective amount of a compound of claim 1.

11. A process for the treatment of epilepsy and anxiety states, which comprises administering to a patient in need therefor an effective amount of a compound of claim 2.

* * * * *